(12) United States Patent
Jansen et al.

(10) Patent No.: US 10,335,245 B2
(45) Date of Patent: Jul. 2, 2019

(54) PACKAGING, PACKAGING ASSEMBLY, AND METHOD FOR USING THE SAME

(71) Applicant: Ossur Iceland ehf, Reykjavik (IS)

(72) Inventors: Marcel Jansen, Reykjavik (IS); Liza A. Boon, Reykjavik (IS); Karim De Waard, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 15/586,496

(22) Filed: May 4, 2017

(65) Prior Publication Data

US 2017/0319286 A1 Nov. 9, 2017

Related U.S. Application Data

(60) Provisional application No. 62/419,121, filed on Nov. 8, 2016, provisional application No. 62/331,503, filed on May 4, 2016.

(51) Int. Cl.
*A61B 50/30* (2016.01)
*B65D 77/22* (2006.01)
*B65D 77/30* (2006.01)
*B65D 85/00* (2006.01)

(52) U.S. Cl.
CPC .............. *A61B 50/30* (2016.02); *B65D 77/22* (2013.01); *B65D 77/30* (2013.01); *B65D 85/00* (2013.01); *A61B 2050/3011* (2016.02)

(58) Field of Classification Search
CPC . A61B 50/30; A61B 50/33; A61B 2050/3011; B65D 77/22; B65D 77/30; B65D 85/00

USPC ............................................. 206/232, 459.5
See application file for complete search history.

(56) References Cited

U.S. PATENT DOCUMENTS

| | | | |
|---|---|---|---|
| 1,562,454 A | 11/1925 | Jenkins |
| 3,011,494 A | 12/1961 | McGowan |
| 3,127,087 A | 3/1964 | Spees |
| 3,216,417 A | 11/1965 | Posey |
| 3,279,459 A | 10/1966 | Schenker |

(Continued)

FOREIGN PATENT DOCUMENTS

| | | |
|---|---|---|
| EP | 0931732 A1 | 7/1999 |
| WO | 9401071 A1 | 1/1994 |

OTHER PUBLICATIONS

International Search Report from PCT Application No. PCT/US2017/030988, dated Jun. 30, 2017.

*Primary Examiner* — Bryon P Gehman
(74) *Attorney, Agent, or Firm* — Workman Nydegger

(57) ABSTRACT

A packaging assembly is arranged for holding an article at a predetermined location relative to the packaging assembly in closed and open configurations of the packaging assembly. The packaging assembly includes at least two sections arranged to be secured in place relative to one another in the closed configuration of the packaging assembly, and move relative to one another in the open configuration of the packaging assembly. The at least two sections form an inner surface defining an attachment area for receiving the article. The packaging assembly includes at least one instruction area located along the inner surface and having indicia pointing to features of an article for placement in the packaging assembly and displayed relative to the attachment area.

18 Claims, 8 Drawing Sheets

(56) References Cited

U.S. PATENT DOCUMENTS

| | | | |
|---|---|---|---|
| 3,485,349 A | 12/1969 | Chaney, Jr. | |
| 3,490,450 A | 1/1970 | Gardner | |
| 3,535,409 A | 10/1970 | Rohde | |
| 3,554,436 A | 1/1971 | Palmer | |
| 3,608,566 A | 9/1971 | Storandt | |
| 3,648,704 A | 3/1972 | Jackson | |
| 3,674,023 A | 7/1972 | Mann | |
| 3,693,619 A | 9/1972 | Williams | |
| D225,472 S | 12/1972 | Lowrey et al. | |
| 3,721,237 A | 3/1973 | Alessio | |
| 3,770,122 A | 11/1973 | Thiele | |
| 3,873,735 A | 3/1975 | Chalin et al. | |
| 3,905,135 A | 9/1975 | Debusk | |
| D239,058 S | 3/1976 | Gaylord, Jr. et al. | |
| 3,955,565 A | 5/1976 | Johnson, Jr. | |
| 4,135,504 A | 1/1979 | Spann | |
| 4,139,643 A | 2/1979 | Hix et al. | |
| 4,186,738 A | 2/1980 | Schleicher et al. | |
| 4,246,288 A | 1/1981 | Sanborn, Jr. | |
| 4,266,298 A | 5/1981 | Graziano | |
| 4,279,344 A | 7/1981 | Holloway, Jr. | |
| D261,821 S | 11/1981 | Hubbard et al. | |
| D268,365 S | 3/1983 | Malkin | |
| 4,433,680 A | 2/1984 | Yoon | |
| 4,433,780 A * | 2/1984 | Ellis | B42D 15/022 206/232 |
| 4,441,493 A | 4/1984 | Nirschl | |
| 4,573,482 A | 3/1986 | Williams, Jr. | |
| 4,597,395 A | 7/1986 | Barlow et al. | |
| 4,598,826 A | 7/1986 | Shinbach | |
| 4,624,244 A | 11/1986 | Taheri | |
| 4,730,610 A | 3/1988 | Graebe | |
| RE32,680 E | 5/1988 | Pompa | |
| 4,781,133 A | 11/1988 | Hanyu et al. | |
| 4,893,617 A | 1/1990 | Bartial et al. | |
| 4,903,841 A | 2/1990 | Ohsima et al. | |
| 4,947,834 A | 8/1990 | Kartheus et al. | |
| 4,968,542 A | 11/1990 | Gasper et al. | |
| 4,972,832 A | 11/1990 | Trapini et al. | |
| 5,002,047 A | 3/1991 | Sandvig et al. | |
| 5,007,418 A | 4/1991 | Bartizal et al. | |
| 5,052,128 A | 10/1991 | Lonardo | |
| 5,195,945 A | 3/1993 | Sandvig et al. | |
| 5,203,764 A | 4/1993 | Libbey et al. | |
| 5,226,245 A | 7/1993 | Lamont | |
| D338,067 S | 8/1993 | Luber et al. | |
| D343,002 S | 1/1994 | Gauvry | |
| 5,288,286 A | 2/1994 | Davis et al. | |
| D352,381 S | 11/1994 | Rose | |
| 5,367,789 A | 11/1994 | Lamont | |
| 5,435,009 A | 7/1995 | Schild et al. | |
| 5,449,339 A | 9/1995 | Drennan | |
| 5,464,385 A | 11/1995 | Grim | |
| 5,479,471 A | 12/1995 | Buckland | |
| 5,505,305 A | 4/1996 | Scholz et al. | |
| 5,511,552 A | 4/1996 | Johnson | |
| D370,728 S | 6/1996 | Edgar et al. | |
| 5,588,954 A | 12/1996 | Ribando et al. | |
| 5,613,779 A | 3/1997 | Niwa | |
| 5,620,095 A | 4/1997 | Delmore et al. | |
| 5,626,556 A | 5/1997 | Tobler et al. | |
| 5,649,954 A | 7/1997 | McEwen | |
| 5,660,182 A | 8/1997 | Kuroshaki et al. | |
| 5,681,115 A | 10/1997 | Diederich et al. | |
| 5,687,848 A | 11/1997 | Scholz et al. | |
| 5,704,480 A | 1/1998 | Scholz et al. | |
| 5,827,211 A | 10/1998 | Sellinger | |
| 5,833,639 A | 11/1998 | Nunes et al. | |
| 5,868,690 A | 2/1999 | Eischen, Sr. | |
| D410,746 S | 6/1999 | Klein | |
| 5,984,088 A | 11/1999 | Dietz et al. | |
| 5,984,092 A * | 11/1999 | Heard-Willmon | A45C 13/02 206/232 |
| 6,080,120 A | 6/2000 | Sandman et al. | |
| 6,126,008 A * | 10/2000 | Cox | B65D 75/22 206/779 |
| 6,126,627 A | 10/2000 | Brennan | |
| 6,152,893 A | 11/2000 | Pigg et al. | |
| 6,277,087 B1 | 8/2001 | Hess et al. | |
| 6,308,713 B1 | 10/2001 | Coleman | |
| 6,318,893 B1 | 11/2001 | Gates | |
| 6,322,530 B1 | 11/2001 | Johnson, Jr. et al. | |
| 6,338,723 B1 | 1/2002 | Carpenter et al. | |
| D453,969 S | 2/2002 | Callsen et al. | |
| D455,836 S | 4/2002 | Lammers | |
| D464,257 S | 10/2002 | Gates | |
| 6,530,477 B1 | 3/2003 | Martorano et al. | |
| 6,550,226 B1 | 4/2003 | Gates et al. | |
| 6,572,573 B1 | 6/2003 | Klein | |
| 6,640,810 B1 | 11/2003 | Callsen et al. | |
| 6,742,321 B2 | 6/2004 | Gates | |
| 6,846,551 B2 | 1/2005 | Genske et al. | |
| 6,926,149 B2 | 8/2005 | Tippey | |
| 7,004,920 B2 | 2/2006 | Fareed | |
| D517,306 S | 3/2006 | Hoeft | |
| 7,052,479 B2 | 5/2006 | Drennan | |
| 7,115,105 B2 | 10/2006 | Cropper | |
| D542,921 S | 5/2007 | Ponsi et al. | |
| D544,101 S | 6/2007 | Kistner | |
| 7,252,647 B1 | 8/2007 | Hely | |
| D551,354 S | 9/2007 | McBarnett et al. | |
| 7,276,037 B2 | 10/2007 | Ravikumar | |
| 7,329,232 B2 | 2/2008 | Lipshaw et al. | |
| 7,353,949 B2 | 4/2008 | Osterdahl et al. | |
| D571,083 S | 6/2008 | Mohammad | |
| 7,455,651 B2 | 11/2008 | Mollica | |
| 7,458,948 B2 | 12/2008 | Drennan | |
| 7,470,062 B2 | 12/2008 | Moteki et al. | |
| 7,758,484 B2 | 7/2010 | Peterson | |
| 7,798,984 B2 | 9/2010 | Ponsi et al. | |
| 7,967,139 B2 * | 6/2011 | Brinker | A61B 50/30 206/472 |
| 8,152,749 B2 | 4/2012 | Ponsi et al. | |
| 8,216,165 B2 | 7/2012 | Ravikumar et al. | |
| 8,241,263 B2 | 8/2012 | Mills | |
| 8,251,932 B2 | 8/2012 | Fout | |
| 8,435,199 B2 | 5/2013 | Ponsi et al. | |
| D697,628 S | 1/2014 | Drey et al. | |
| D703,064 S | 4/2014 | Warrington et al. | |
| 8,951,590 B2 | 2/2015 | Hatinger et al. | |
| D731,158 S | 6/2015 | Backus | |
| 9,241,873 B2 * | 1/2016 | Upchurch | A61J 1/035 |
| D749,744 S | 2/2016 | Drey et al. | |
| 9,271,860 B2 | 3/2016 | Romo | |
| 9,452,878 B2 * | 9/2016 | Baker | A43D 3/1408 |
| 9,561,889 B2 | 2/2017 | Dayrit et al. | |
| 9,642,559 B2 * | 5/2017 | Falconio-West | A61B 5/6828 |
| 2001/0051240 A1 | 12/2001 | Denis | |
| 2003/0168063 A1 | 9/2003 | Gambone et al. | |
| 2004/0111048 A1 | 6/2004 | Jensen et al. | |
| 2004/0236261 A1 | 11/2004 | McCarthy et al. | |
| 2005/0131321 A1 | 6/2005 | Ravikumar | |
| 2005/0171461 A1 | 8/2005 | Pick | |
| 2005/0192524 A1 | 9/2005 | Lipshaw et al. | |
| 2007/0032773 A1 | 2/2007 | Magee | |
| 2007/0074427 A1 | 4/2007 | Ponsi et al. | |
| 2007/0209957 A1 | 9/2007 | Glenn et al. | |
| 2008/0022559 A1 | 1/2008 | Ponsi et al. | |
| 2009/0076427 A1 | 3/2009 | Ponsi et al. | |
| 2009/0149791 A1 | 6/2009 | Ponsi et al. | |
| 2009/0227927 A1 | 9/2009 | Frazer | |
| 2010/0078347 A1 | 4/2010 | Brinker | |
| 2010/0082060 A1 | 4/2010 | Avitable | |
| 2010/0152638 A1 | 6/2010 | Ponsi et al. | |
| 2010/0312160 A1 | 12/2010 | Creighton et al. | |
| 2010/0324517 A1 | 12/2010 | Lenhult et al. | |
| 2011/0125183 A1 | 5/2011 | Lipshaw et al. | |
| 2011/0180074 A1 | 7/2011 | Gainey | |
| 2012/0012118 A1 | 1/2012 | Ponsi et al. | |
| 2012/0179082 A1 | 7/2012 | Ponsi et al. | |
| 2012/0193957 A1 | 8/2012 | Grover | |
| 2012/0209158 A1 | 8/2012 | Avitable et al. | |
| 2013/0085427 A1 | 4/2013 | Malhi | |

(56) References Cited

U.S. PATENT DOCUMENTS

| | | |
|---|---|---|
| 2013/0085432 A1 | 4/2013 | Malhi et al. |
| 2014/0107546 A1 | 4/2014 | Falconio-West et al. |
| 2014/0107547 A1 | 4/2014 | Drey et al. |
| 2014/0173940 A1 | 6/2014 | Drennan |
| 2014/0194796 A1 | 7/2014 | Noskowicz et al. |

* cited by examiner

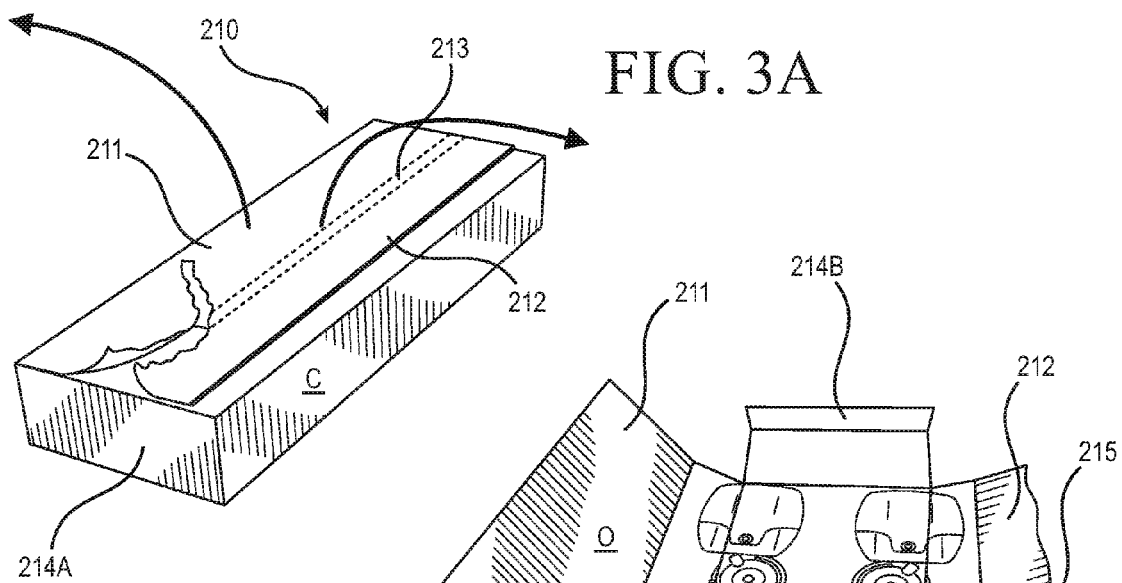
FIG. 3A
FIG. 3B
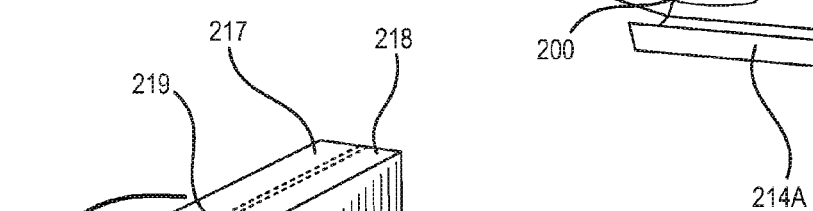
FIG. 4A
FIG. 4B

PACKAGING, PACKAGING ASSEMBLY, AND METHOD FOR USING THE SAME

FIELD OF THE DISCLOSURE

The disclosure relates generally to a packaging assembly arranged for placement of an article in a predetermined configuration, packaging having instructional indicia for using the article, and packaging for placing the article in the predetermined configuration. Methods and packaging assemblies for using the packaging with an article are likewise provided in the disclosure. In an exemplary form, the packaging assembly is described as a donning aid packaging.

BACKGROUND

Articles are packaged in different ways depending on shipment, storage, use of the article, and other reasons. As frustration may occur with such packaging, and the lack of the packaging being user friendly for quick and efficient usage of an article stored therein, there is an effort to provide packaging that facilitates easy removal of an article. In an example of orthopedic devices delivered to many locations across different countries, it is desirable to provide packaging efficient for space, instructional for instant usage of the orthopedic device, intuitive, and simple to remove the orthopedic device.

With orthopedic devices, there are typically steps and procedures that must be followed to properly don an orthopedic device. Often an orthopedic device must be opened from the packaging it is shipped and contained in, assembled, positioned upon the wearer, and adjusted to properly fit the wearer. Whether this is done by the wearer or by a treating physician, nurse, therapist, assistant or other caretaker (collectively referred to as a "clinician"), there is risk that the orthopedic device will be misapplied or improperly adjusted, reducing the effectiveness of the orthopedic device or leading to misuse by the wearer.

Even if the orthopedic device is properly fit to the wearer and adjusted correctly, the time to remove the orthopedic device from its packaging, preparing or assembly, positioning upon the wearer, or adjusting on the wearer can be lengthy. Often, a wearer or even a more experienced caretaker can become confused by the multitude of straps, couplings, guides, pads, locks, and other interrelated components of the orthopedic device, which must be properly configured in a specific manner to achieve proper use of the orthopedic device.

Orthopedic braces are received with printed instructions and/or instructions are made available online, through instructions for use ("IFU") or instructional videos, or available in a small booklet provided along with packaging. However, even with such instructions it often requires the wearer or person fitting the device to iterate between reading the instructions, examining and manipulating the device, and reading the instructions again. Where a wearer or person fitting the device has full comprehension of the instructions, the arrangement of the pre-packaged device still requires preparation or assembly of the device in a manner that matches the instructions. This often requires the manipulation of many straps, couplings, adjustable features, and other components.

An orthopedic device may include areas of hook and loop fastener material, particularly in relation to straps intended to secure the device to the wearer. To fit such an orthopedic device, a person doing the fitting must properly arrange all the straps. This can be challenging as the hook and loop fastener materials stick and attach at improper positions without careful handling, which can lead to tangling of the straps. Where a multitude of straps are included, as is often the case and with donning the device, the straps may be arranged and manipulated in a proper sequence. Several unnecessary steps of attaching, detaching, readjusting, and reattaching may be cycled through to obtain a proper fit.

Orthopedic devices may be packaged in bags which are placed in containers. Using a bag in a container leads to the orthopedic device shifting while in transit, and makes it difficult to arrange the orthopedic device in an initial, predetermined configuration for donning. The bags and containers lead to waste, as often general purpose sized containers are used for placement of the orthopedic device. From this, inventory of the orthopedic devices in containers takes considerable and unnecessary space.

There is need for an orthopedic device packaging that can package an orthopedic device while also being capable of functioning as a donning aid. It is desirable to have an orthopedic device packaging that reduces or eliminates drawbacks related to lengthy preparation/assembly times and fitting times of the packaged orthopedic device. It is also desirable to have an orthopedic device packaging capable of arranging the packaged orthopedic device in a manner that minimizes the potential for confusion for the person fitting the device, and that reduces the number of steps required to properly don the device in a clear and efficient manner by eliminating booklets and online searching for understanding how to properly don the orthopedic device. Further yet, it is desired to provide packaging that eliminates waste and reduces inventory space.

SUMMARY

Embodiments relate to packaging arranged for placement of an article in a predetermined configuration and packaging having instructional indicia for using the article and corresponding to the article in the predetermined configuration. In a specific embodiment, the packaging is arranged as a donning aid packaging assembly.

Regarding orthopedic devices as an exemplary article, a donning aid packaging assembly advantageously aids a wearer (e.g., a physician, clinician or other caretaker, or the wearer him/herself) in properly fitting an article, such as an orthopedic device. Embodiments disclosed herein package the orthopedic device in a manner such that, upon opening the packaging, the orthopedic device is presented in an open manner and is provided for positioning upon the wearer.

It is understood that an orthopedic device is described as an exemplary article for being used in combination with the packaging embodiments, and the embodiments envision other articles that may be packaged in combination with general features of the packaging embodiments.

The packaging is moveable (e.g., foldable, unfoldable) from a housing structure that supports the orthopedic device to an expanded structure that presents the orthopedic device upon a display surface. The display surface includes indicia instructing a wearer as to the proper donning of the orthopedic device. In certain embodiments, the instructions include sequence instructions directly pointing toward corresponding components of the orthopedic device to instruct a wearer on the proper sequence by which the device components should properly don the device.

Embodiments of the packaging may include retaining elements for maintaining the orthopedic device in a prearranged configuration so that upon opening of the packaging, the orthopedic device is provided for simple donning under a sequence of instructions provided directly on the packaging. As preferred embodiments may require a donning sequence, indicia for understanding the sequence of components may be provided with lead lines pointing directly to components of the orthopedic device. Instructional images may correspond and be located adjacent the indicia to show steps for installing the orthopedic device. Advantageously, the images may enable a reduction of instructions and provide picture instructions that do not require languages, as the orthopedic device may be sold in different countries with different languages.

The packaging is streamlined in the sense it reduces waste and inventory space. The packaging is arranged with markings and instructions built-in to eliminate the need for booklets and online searching. Elements may be provided in combination with the packaging to maintain the article in a predetermined configuration. The packaging may be arranged so it is in a soft package, such as packaging without hard edges and structure, or hard packaging, such as packaging retaining a predetermined shape. The packaging may be arranged in larger packaging but in a manner that minimizes space and facilitates organization of products in the packaging.

In an embodiment of the packaging assembly, it is arranged for holding an article in closed and open configurations of the packaging assembly. The packaging assembly includes at least two sections arranged to be secured in place relative to one another in the closed configuration of the packaging assembly. The at least two sections are adapted to move relative to one another in the open configuration of the packaging assembly. The at least two sections form an inner surface defining an attachment area for receiving the article.

The at least two sections may comprise panels attached to one another or a unitary structure formed from a single panel but further divided into sections of subpanels according to creases or other forms for delineating sections of the single panel. The at least two sections may be formed from a flexible bag or sheet, and are joined to one another. Other packing materials, containers and substrates may form the at least two sections, particularly materials, containers or substrates that can close to form an enclosure, and open into a generally flat or otherwise contoured shape or shapes for facilitating donning of an article.

At least one instruction area is preferably located along the inner surface of the at least two sections and has indicia pointing to features of the article for placement in the packaging assembly and displayed in a spatial relationship relative to the attachment area. The at least one instruction area is preferably printed onto the inner surface of the at least two sections, and is arranged for accommodating a specific article since the instruction area has lead lines intended to point to specific features of the article. Therefore the attachment area should be arranged to repeatedly place the article at a specific location, and secure the article relative to the attachment area so the at least one instruction area aligns with the article in the packaging assembly.

A fastener may be within the attachment area and secured to the article within the attachment area in both the closed and open configurations. It is preferable that the article is arranged in an open configuration for facilitating donning of the article when the packaging assembly is in an open configuration. By securely retaining the article in the closed and open configurations, the article can be set in position upon opening of the packing assembly for easy donning. While the fastener should secure the article relative to the packing assembly, it is preferably arranged for easy detachment from the attachment area when the article is donned onto the wearer.

The attachment area is preferably generally centrally formed among the at least two sections and includes a marking for placing the article and a feature thereof at the marking. While the attachment area can be placed askew to a central location of the packing assembly depending on the configuration of the packaging assembly or article, in the embodiment whereby it is generally centrally formed, such as in a post-operative knee brace, the packaging assembly can be located under the leg of a wearer, and accommodate opposed lengths of straps or buckles for easy donning onto the wearer's leg.

According to an embodiment of the packaging assembly, the packaging assembly includes a longitudinal seam or closure running along a longitudinal axis of a top face of the packaging assembly and securing the at least two sections together. A closure or closures may be located along sides or other suitable locations according at least to the application of the article and configuration of the packaging assembly. In the open configuration of the packaging assembly and upon opening of the closure, the at least two sections open in a bi-fold fashion. The at least two sections may include hinges, creases or folds that facilitate the bi-fold manner of opening the packaging assembly. In another alternative, the packaging assembly includes a transverse closure generally extending transversely to the longitudinal axis along transverse edges of the at least two sections.

In a variation, the at least two sections may have features arranged for aiding the transport and handling of the packaging assembly. The at least two sections may join in the closed configuration to form a handle.

The packaging assembly may be formed so that the at least two sections define first and second side panels and a central panel. The central panel can be rigid or semi-rigid, or otherwise formed to maintain a predetermined distance between the first and second side panels. Preferably, the attachment area is arranged so it coincides with the central panel.

The indicia of the at least one instruction area is preferably directly located on and/or along the inner surface of the at least two sections. The indicia may be printed directly onto the at least two sections. The indicia may be provided on a liner secured to the at least two sections so the liner does not shift and can be maintained to point the indicia to features of the article.

The at least one instruction area may define lead lines located on or otherwise about the at least two sections, and which align the indicia to features of the article. Such indicators permit the wearer and clinician to know which of the features of the article to employ without the necessity of viewing an instructions-for-use manual while donning the device. The indicia and lead lines may be non-language specific, and universal so the same packaging can be advantageously used for multiple individuals across different languages.

In an example, the indicia is arranged on the at least two sections in a sequential manner corresponding to sequential features of the article. The sequential manner may relate to steps for donning the article, and can be presented with numbers, lettering or other symbols that easily and quickly convey to the clinician and wearer how and the order by which the article should be secured to the wearer. Advantageously the wearer or clinician need only look at the article and proximate indicia while donning which leads to the synergistic effect of eliminating instruction manuals and assuring without doubt how best to secure the article onto the wearer.

Additional aids to the mere at least two sections may aid in donning the article. In an example, a positioning element connects to the at least two sections and is adapted to maintain an article in a fixed position relative to the at least two sections.

In an exemplary method for donning an article, steps may include placing the article in a packing assembly, as in the aforementioned embodiments and variations thereof, having at least two sections arranged to be secured in place relative to one another in a closed configuration, and move relative to one another in an open configuration. The at least two sections may form an inner surface defining an attachment area for receiving the article. The article can be placed in the attachment area, and at least one instruction area is located along the inner surface and has indicia pointing to features of the article.

The indicia is located on the inner surface, and comprises at least two indicators arranged in sequential notation pointing to different features of the article. A first indicator is presented and a first feature of the article is donned first and corresponds to the first indicator. Subsequently, a second feature corresponding to a second indicator may be donned.

Prior to opening the packaging assembly, the at least two sections may be secured to one another along at least their edges.

A packaging assembly may contain an article secured at a predetermined location relative to the packing assembly in closed and open configurations of the packaging assembly. In combination with the article, the packaging assembly includes at least two sections arranged to be secured in place relative to one another in the closed configuration, and move relative to one another in the open configuration. The at least two sections form an inner surface defining an attachment area upon which the article is secured. At least one instruction area is located along the inner surface and has indicia pointing to features of an article for placement in the packaging assembly. The at least one instruction area is preferably located relative to an attachment area displayed by the at least two sections and the article has a feature corresponding to and secured to the attachment area at a marking in both the closed and open configurations. At least one closure is arranged to secure edges of the at least two sections to one another in the closed configuration. The indicia preferably represents a sequence of steps for utilizing a sequence of features of the article. The article is secured to the at least two sections such that the article is stabilized in the open configuration of the packing assembly in an open configuration of the article.

BRIEF DESCRIPTION OF THE DRAWINGS

These and other features, aspects and advantages of the aforementioned embodiments will become better understood with regard to the following description, appended claims, and accompanying drawings.

FIG. 3A is a schematic view showing another donning aid packaging in a closed configuration.

FIG. 3B is a schematic view of the donning aid packaging of FIG. 3A in a closed configuration.

FIG. 4A is a schematic view showing another donning aid packaging in a closed configuration.

FIG. 4B is a schematic view showing the donning aid packaging of FIG. 4A in an open configuration.

DETAILED DESCRIPTION OF VARIOUS EMBODIMENTS

Various packing assembly embodiments and methods for using the same are described herein in the exemplary form of a donning aid packaging configured for housing an article, such as an orthopedic device. While the orthopedic device is shown as a post-operative knee brace, it will be understood that similar embodiments and components as described may be used for donning aid packaging housing one or more orthopedic or prosthetic devices in the form of elbow braces, ankle braces, shoulder braces, neck collars/braces, prosthetic devices, or any other orthopedic or prosthetic device. While the term "donning" is frequently used herein for discussing the packaging, the donning aid packaging is not limited to providing instructions for donning articles, but may be extended to other articles requiring a sequence of steps visually displayed in a language-specific or language-neutral manner.

Figure 1A:
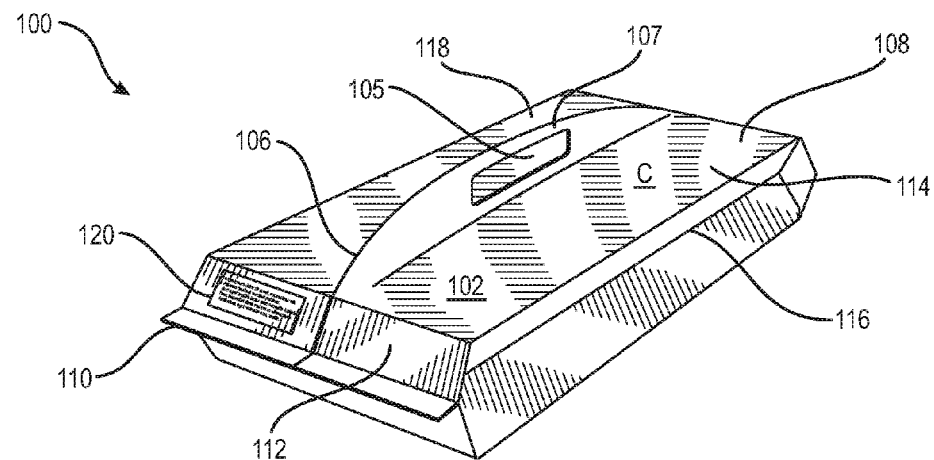
FIG. 1A is a perspective view of an exemplary donning aid packaging in a closed configuration.
Figure 1B:
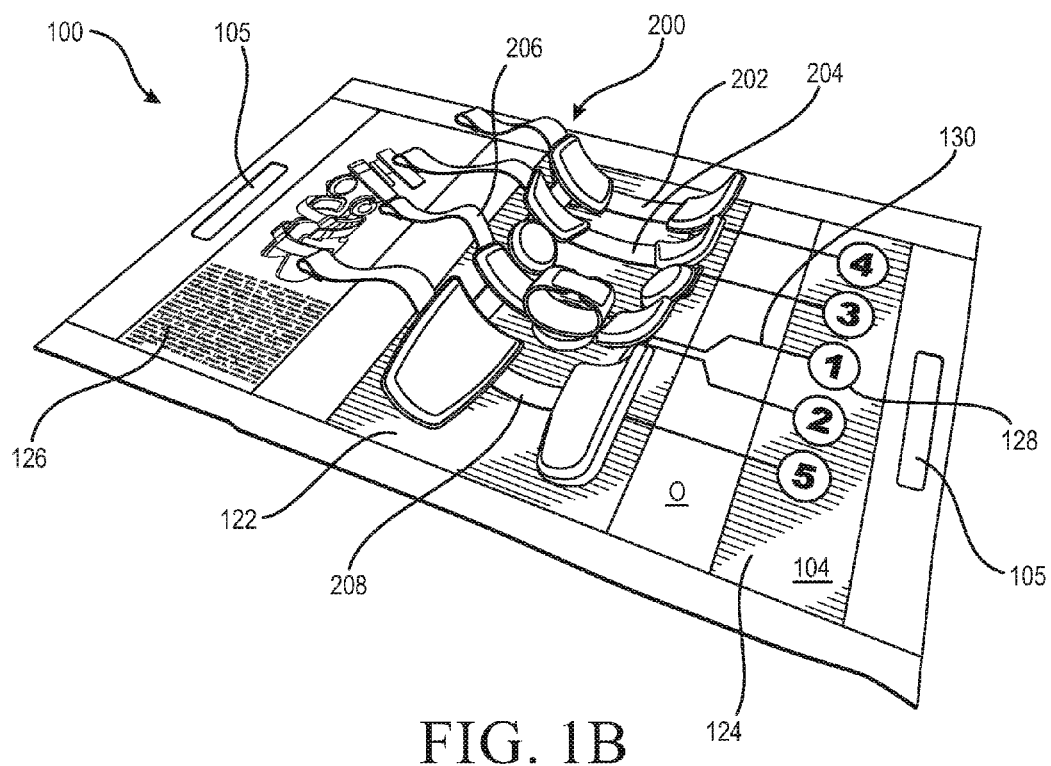
FIG. 1B is a perspective view of the donning aid packaging of FIG. 1A in an open configuration, showing the orthopedic device and the interior components of the donning aid packaging.

FIGS. 1A and 1B illustrate an exemplary donning aid packaging 100 in a closed configuration C with the outer surface 102 of the packaging (FIG. 1A) and an open configuration O with the inner surface 104 of the packaging (FIG. 1B). The donning aid packaging may be formed from any suitable packaging material, either as a soft good without rigid or semi-rigid edges or as a hard good with rigid or semi-rigid edges. In any of the embodiments, the packaging may be recyclable, and due to its minimal and streamlined nature, it eliminates excessive waste.

According to the embodiment of FIG. 1A, preferably, the material is a hard good because it is sufficiently rigid and durable to enable proper housing of an orthopedic device while minimizing unnecessary weight and bulk, and modifies in shape according to the article held by the packaging.

Suitable materials may include cardboard, plastics, and combinations thereof. The packaging may be frustration-free because it comes without excess packaging materials, and may be recyclable. A single opening may be provided to assure the packaging is opened in a predetermined manner to assure the article is presented in a manner consistent with the donning aids.

The illustrated donning aid packaging 100 includes a longitudinal closure or seam 106 running along a longitudinal axis of a top face 108 of the packaging 100, a first side seam 110 running along a first side face 112 of the packaging in a direction transverse to the longitudinal axis, and a second side seam (not shown) running along a second side face (not shown; disposed opposite the first side face 112) in a direction transverse to the longitudinal axis. The seams are configured to enable the packaging 100 to be preferably opened in a bi-fold fashion, such that panel 114 can be opened along hinge 116 and the panel 118 can be opened along a similar hinge (not shown) opposite from hinge 116.

Alternative embodiments can include arrangements of seams and/or hinges to allow for different open configurations O. Some embodiments may be configured such that a single face opens along a single hinge section. Other embodiments may be configured such that a plurality of separate panels (e.g., three, four, or more) separate and open up. Embodiments may be configured such that separate opening panels are non-uniform in size (e.g., a corresponding seam does not run along a centerline of a face of the packaging). Any of the described embodiments may be combined with one another.

As depicted in FIGS. 1A and 1B, the donning aid packaging 100 includes labeling 120 for indicating the type, style, brand, etc. of the prosthetic device housed within the packaging. The handle 107 is formed from two separate apertures 105 such that the apertures 105 align to form the hole of the handle 107 when the packaging 100 is in the closed configuration C.

Shown in FIG. 1B, the packaging 100 is preferably configured to lay flat in an open configuration O. This beneficially allows a clinician to slide the packaging and the orthopedic device 200 under the wearer's leg with ease, and can even free the clinician to do so with one hand while supporting or positioning the wearer's leg with the other hand.

Upon opening the packaging 100, the orthopedic device 200 is displayed. The packaging 100 includes hook material, adhesive material, or other suitable fasteners to hold the orthopedic device 200 and features thereof in position. The straps 202, 204, 206, 208 may include loop fastener materials for attachment to corresponding sections of hook fastener material placed on the attachment area 122 of the packaging. This advantageously aligns the orthopedic device 200 in the proper position relative to a sequence instructions area 124 and detailed instructions area 126.

The sequence instructions area 124 displays instructions that enable a clinician or wearer to properly don the orthopedic device 200 according to the proper procedure. In the illustrated embodiment, the sequence instructions include indicia such as letters or numbers 128, with lead lines 130 pointing to a separate components of the orthopedic device 200 and/or indicating a sequential step to be performed in donning the orthopedic device 200.

The detailed instructions area 126 can include additional instructions for use and/or other device information, such as usage information applicable after the device has been donned. The illustrated embodiment includes a set of detailed instructions in the display area 126 as compared to the relatively simpler instructions in the sequence instructions area 124. This dual mode presentation of instructions beneficially provides multiple depth levels of instructions to suit a variety of wearers. A first time wearer may be more interested in detailed instructions besides the more streamlined instructions, while a wearer that has applied multiple orthopedic devices may just be interested in a relatively simplified reminder about the overall sequence of fitting the particular device 200 to the wearer.

Beneficially, the instructions of the sequence instructions area 124 and the detailed instructions area 126 are preferably displayed immediately adjacent to the same orthopedic device to which they apply. As opposed to a physically separated set of instructions in a booklet, these instructions may be displayed with direct reference to the actual object of the instructions. Rather than basing the instructions solely on text descriptions of the orthopedic device, or even on text descriptions referring to an image of the orthopedic device, one or more of the instructions of the packaging 100 refer and direct to the actual and tangible orthopedic device 200. The numbers of the sequence instructions area 124 are shown in FIG. 1B pointing directly to different components of the actual orthopedic device that the wearer will don.

This arrangement enables a clear presentation and overview of the process for properly donning the orthopedic device 200. Advantageously, this limits the time that must be spent referring to separate instructions and correlating such instructions to the actual orthopedic device to be donned. The sequence instructions ensure that backtracking and undoing of strap attachments and other steps are minimized. This can save clinician time and can reduce the risk that the orthopedic device 200 is donned improperly.

The instructions of the sequence instructions area 124 are shown as numbers directing to components of the orthopedic device 200. Or instructions may include color-coding, text descriptions (preferably less than about 25 words, or less than about 10 words), or images (e.g., showing what a proper buckle attachment should look like). In some embodiments, corresponding components of the orthopedic device 200 are labeled to match the instructions of the sequence instructions area 124. Straps or other components may be colored and/or numbered to correspond to the instructions.

As depicted, the orthopedic device 200 is attached to the packaging 100 so the orthopedic device 200 is opened and ready to be positioned upon the wearer as the packaging 100 is opened. This feature can also save time and simplify the donning process. As compared to a typical pre-packaged orthopedic device, which must first be prepared/assembled before it can be positioned upon the wearer, the orthopedic device 200 is readily positioned upon opening of the packaging 100.

Many orthopedic devices are pre-packaged so that the straps, buckles, and other components are attached and tightened. While this may prevent the straps from tangling and attaching to improper surfaces during shipment and handling, it unavoidably necessitates that all components are undone prior to donning of the device. This adds time and the potential for confusion to the entire donning process, and these limitations are avoided by the donning aid packaging 100.

The illustrated embodiment includes detailed instructions in the detailed instructions area 126 and sequence instructions in the sequence instructions area 124. In other embodiments, such areas are not distinct. Some embodiments may include an arrangement of different pieces of instructions having a sequence instruction (e.g., a number) alongside a corresponding detailed excerpt and/or image more fully describing the particular step.

An embodiment of a donning aid packaging will now be described in relation to the fitting of a particular post-operative knee brace. An example of the post-operative knee brace is found in co-pending U.S. patent application Ser. No. 15/478,478, filed on Apr. 13, 2017, incorporated herein by reference. Although described in this context, other donning aid packaging embodiments may be configured for other orthopedic devices having different components and/or fitting procedures.

A sequence instructions area can display a first instruction (e.g., the number "1"), pointing to a length adjustment component of the brace. The brace may include a number of paddles adjustably attached to struts, with the paddles being adjustable relative to the struts according to the height/leg length of the wearer. The packaging may include an additional text description and/or image to aid in this step (e.g., describing the proper length of the brace relative to the groin and ankle of the patient). Subsequent instructions in the sequence instructions area may then direct to similar length adjusting components so all sections (e.g., medial upper, medial lower, lateral upper, lateral lower) are properly adjusted for length.

In some embodiments, related steps, such as the related length adjustment steps, may be broken down as sub-steps (e.g., "1a," "1b," "1c," "1d," etc.). A subsequent instruction directs a wearer to the struts of the brace. Optionally, the struts may be bent, using bending irons or other suitable tools, to better conform to a wearer's particular leg anatomy.

A subsequent instruction directs a wearer to an anti-migration strap of the brace. The anti-migration strap functions to broaden the strap to urge generally uniform pressure about the circumference of the leg to limit migration. The anti-migration strap is preferably formed from a material that is flexible and breathable and that provides frictional properties, such as a high friction foam material. The anti-migration strap is preferably positioned immediately below the knee above the widest portion of the calf. The packaging may include a diagram and/or descriptive text describing this positioning.

Subsequent instructions direct a wearer to the various straps and strap components of the device. A first strap instruction can direct a wearer to a strap guide located on a first side of the device (e.g., medial side) to direct a wearer to adjust the corresponding strap relative to the strap guide. A subsequent strap instruction can direct a wearer to a strap-coupling member located on a second side of the device (e.g., lateral side) to direct a wearer to couple the strap to the strap-coupling member. A subsequent strap instruction can direct a wearer to a strap-tightening component and/or a strap-securing component for securing the strap after tightening. Subsequent instructions can direct the wearer to various similar strap components to guide the wearer in repeating the process for additional straps of the brace.

A subsequent instruction directs a wearer to a pivot assembly to enable the wearer to set the pivot assembly at appropriate flexion and extension settings. The pivot assembly functions to limit the wearer's range of motion in both flexion and extension directions. A subsequent instruction or sub-instruction then directs a wearer to a pivot assembly on the opposite side to ensure that each pivot assembly is appropriately configured.

Figure 2A:
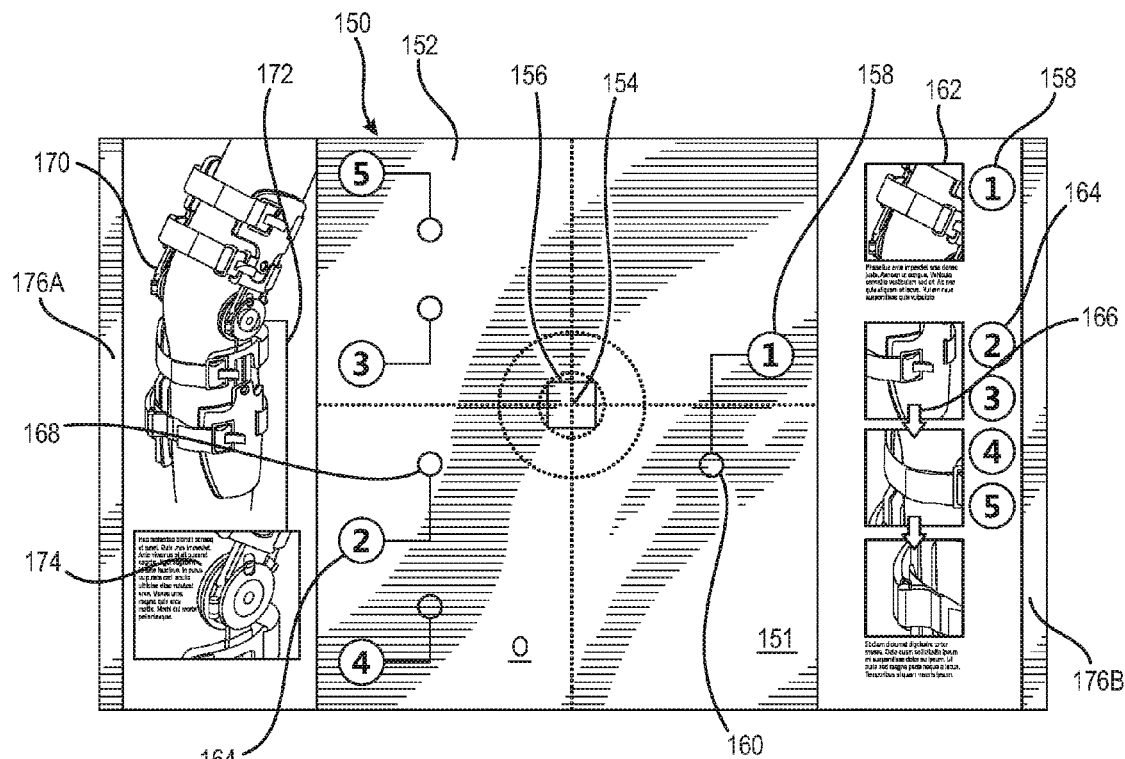
FIG. 2A is a plan view of another embodiment of the donning aid packaging as a soft package in an open configuration.
Figure 2B:
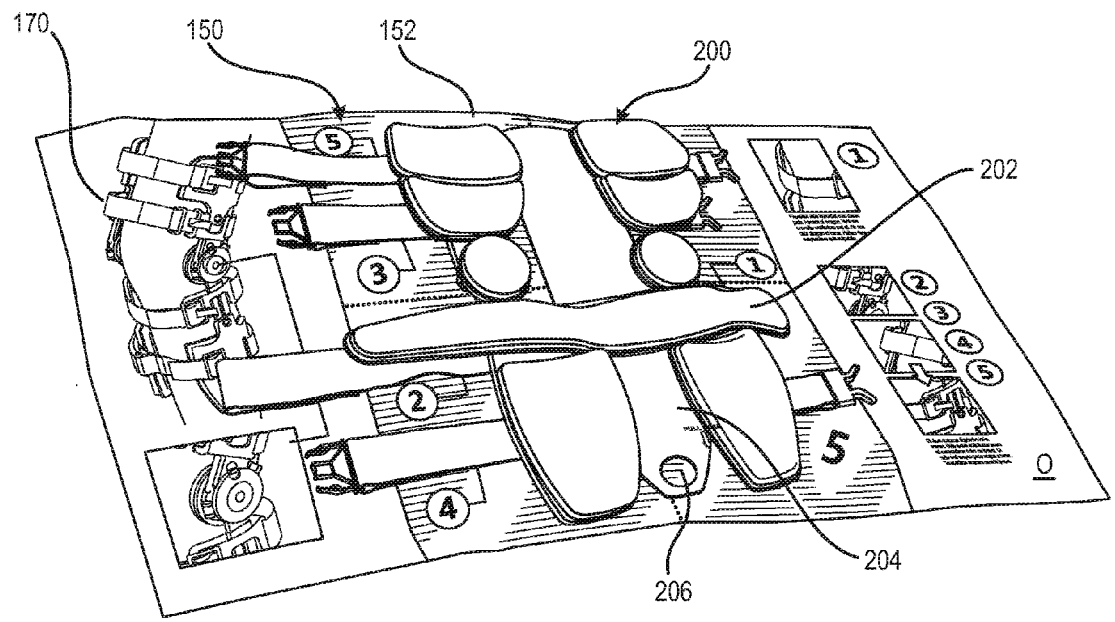
FIG. 2B is a perspective view of the donning aid packaging of FIG. 2A in the open configuration, showing an article located thereon.

FIGS. 2A and 2B show another embodiment of the packaging 150 in an open configuration O. According to this embodiment, the packaging is a considered a soft good because it is flexible and may yield to the shape of the article, as in the orthopedic device 200. Nonetheless, the flexible packaging may be considered to have at least two panels or sections 151 which fold generally along a center-line or other suitable crease for folding or retaining the article so it can be easily donned when the packaging is in the open configuration O. The flexible packaging may be considered as having first and second panels and a center panel, as in the embodiments of FIGS. 1B and 4D, although the flexible packaging is flexible whereas the aforementioned embodiments may have stiffer and more delineated sections or panels.

The packaging may be a sealed pouch containing the article. The sealed pouch may be arranged to assure that the article is sterile prior to use, and the packing assembly has not been tampered with prior to the initial donning. The seal pouch may be hermetically sealed to assure that the article is preserved in a medical or other use satisfactory state prior to donning. Such desirability and arrangements may be done in any of the embodiments discussed herewith. The closures, such as seals, for the packaging assembly may include tamper evident means, as understood by one having ordinary skill in the art, to assure the packing assembly has not been opened prior to the first use.

The packaging 150 has an inner surface 152 that can be laid planar to attach the orthopedic device. The inner surface 152 defines markings 154, such as a crosshair for placement of the orthopedic device. Fasteners, glue, wire ties, tape or other suitable means may mount the orthopedic device relative to the markings 154 and maintain the orthopedic device in place. A hook and loop fastener 156 may be mounted centrally relative to the markings for securing the orthopedic device thereon with corresponding fasteners. Fasteners may be provided at other suitable locations along the inner surface according to the shape and configuration of the article.

As in the previous embodiment of FIGS. 1A and 1B, indicia including an indicator 158 may be printed or otherwise located directly on the inner surface 152 along with leader lines 160 pointing to the exact feature of the orthopedic device. Images 162 of the orthopedic device are provided along with the corresponding indicia 158 along the side of the orthopedic device. Likewise, additional sequential indicators 164 and leader lines 168 are provided with images 162 and signs 166 for showing next steps to in a language neutral manner or eliminate the need for language to be used to show the wearer what to do. Imagery of the orthopedic device 170 may be provided with language or language neutral markings, such as an image, text or both 174, with a leader line 172 pointing to a specific configuration of the orthopedic device 170.

FIG. 2B shows how positioning elements, in addition to or replacing fasteners, are used to maintain the orthopedic device in a predetermined configuration. The positioning element 204 may be a board that maintains the orthopedic device in an open configuration O to mitigate bunching or tangling of straps, and facilitate donning of the orthopedic device. U.S. Pat. No. 9,271,860, granted Mar. 1, 2016, and incorporated herein by reference, explains the importance of maintaining an orthopedic device, in a post-operative knee brace. The positioning element 204 maintains first and second struts in a generally flat configuration relative to one another and enables a curved configuration upon application of a load on the first and second struts. The positioning element 204 defines an opening 206 for easily pulling the positioning element 204 from the orthopedic device. Strapping 202 of the orthopedic device 200 may be placed over the positioning element 204 for making donning of the orthopedic device 200 easier and under the prescribed set of procedures.

Figure 2C:
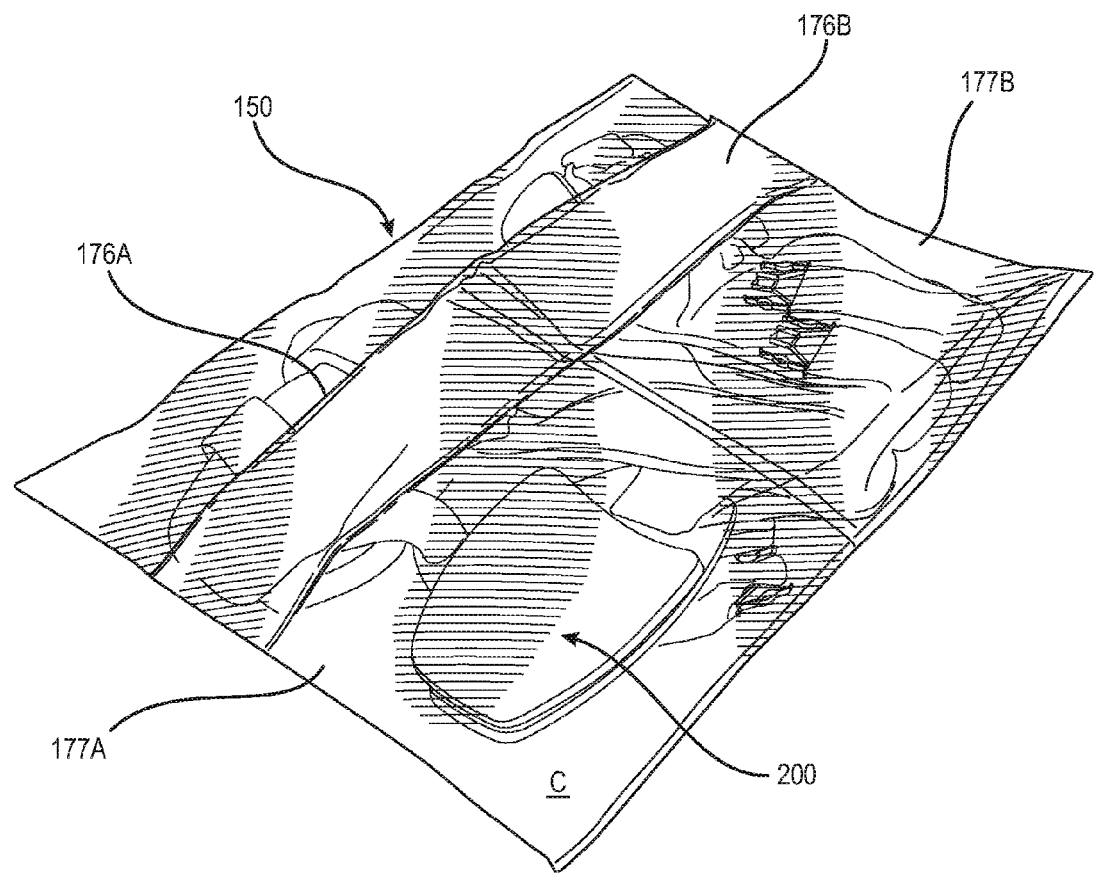
FIG. 2C is a schematic view showing the donning aid packaging of FIG. 2A in a closed configuration.

FIG. 2C shows the packaging in a closed configuration C whereby lateral edges 176A, 176B, and longitudinal edges 177A, 177B seal to enclose the orthopedic device. A clinician may cut or pull apart the lateral edges 176A, 176B along their connection to open the packaging and withdraw the orthopedic device 200, so it is in the configuration, as shown in FIG. 2B.

FIGS. 3A and 3B illustrate a donning aid packaging 210 arranged as a hard good, but with simple access for retrieving the orthopedic device 200. Specifically, opposed lateral sides 211, 212 are joined by a tear strip 213 and bounded by longitudinal enclosures 214A, 214B. Upon tearing the tear strip 213, a clinician can open the packaging 210 so the orthopedic device is in the correct position for retrieval and donning on a wearer. At least one of the lateral sides 211, 212 may be severed with a roughened edge 215 by removal of the tear strip 213, with the longitudinal edges 214A, 214B opening up for access to the orthopedic device 200. The packaging may be arranged with any of the foregoing features for assisting donning of the orthopedic device 200, so the orthopedic device is immediately ready for use.

Whereas the packaging 210 in FIGS. 3A and 3B is in a flat or wide configuration, the donning aid packaging 216 of FIGS. 4A and 4B, is in a tall or upright configuration. The packaging 216 includes opposed shortened lateral sides 217, 218 joined by a tear strip 219. Removal of the tear strip 219 opens the packaging 216, and at least one of the lateral sides 217, 218 has a roughened edge 221. As in the former embodiments, the orthopedic device is arranged in a manner that facilitates quick and easy donning. This arrangement may be a compact box.

Figure 4C:
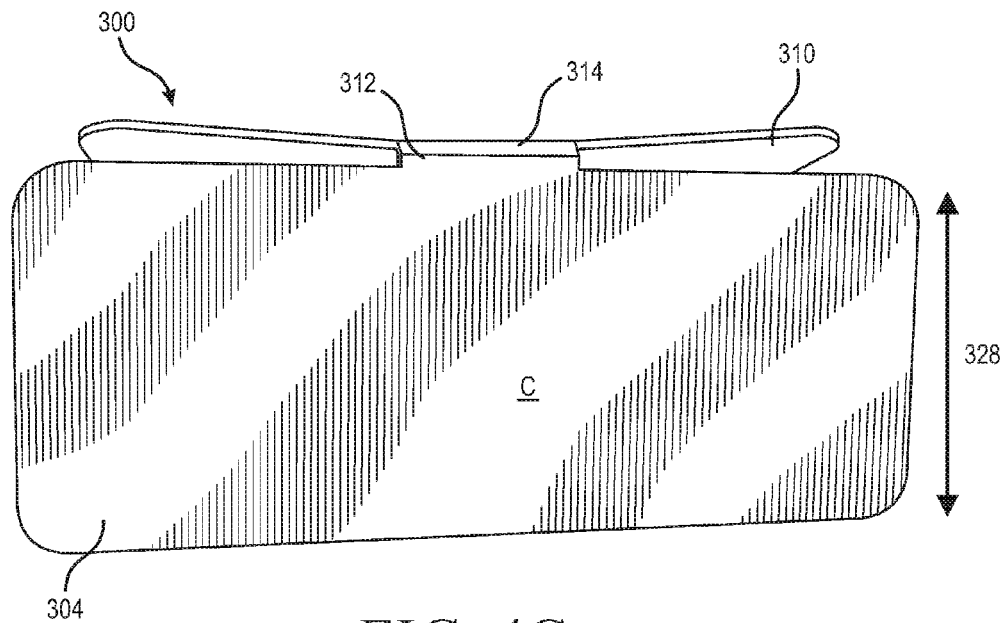
FIG. 4C is a schematic view of another embodiment of donning aid packaging in a closed configuration.
Figure 4D:
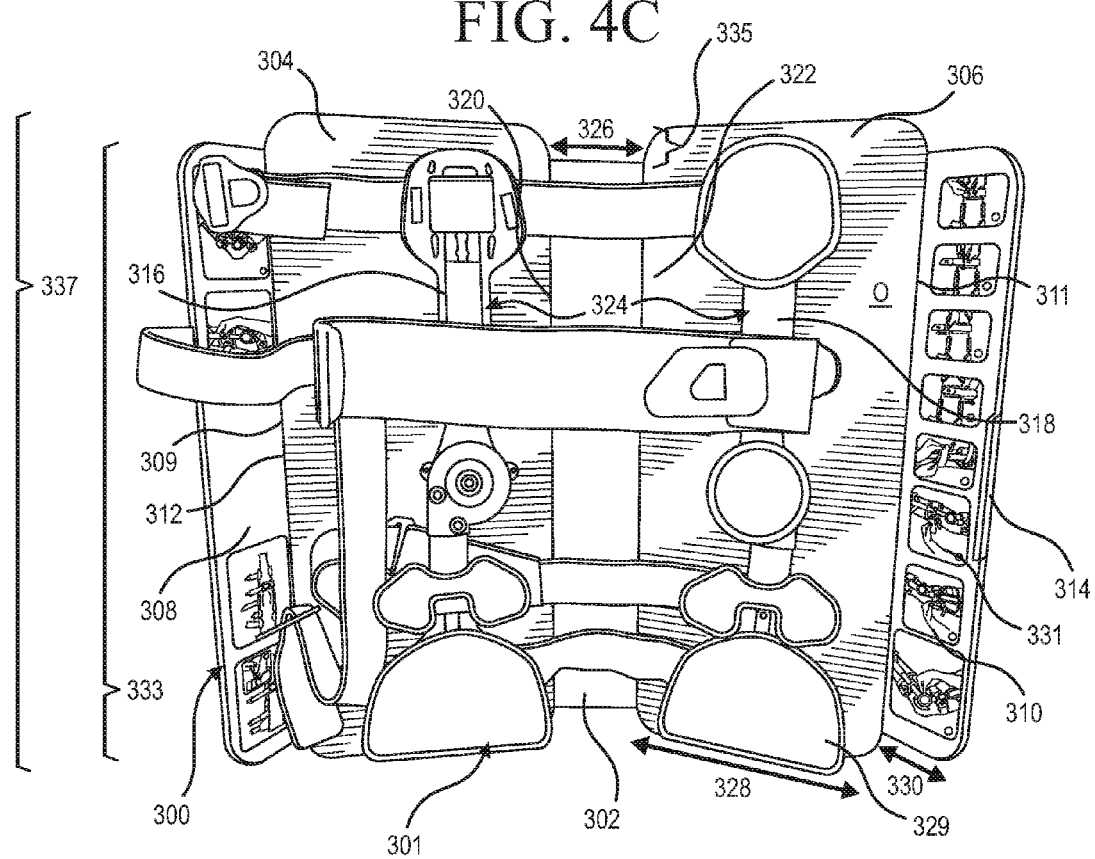
FIG. 4D is a schematic view of the donning aid packaging of FIG. 4C in an open configuration.

FIGS. 4C and 4D exemplify another embodiment of compact donning aid packaging 300 for an orthopedic device that enables ready positioning of the orthopedic device for donning an orthopedic device 301. The packaging 300 is sufficiently compact to permit the packaging to be insertable under a wearer's limb, and is of sufficient size to be contained within a bag or a pouch to take little storage space while protecting the orthopedic device contained therein.

In this embodiment, the packaging 300 is preferably formed by a continuous board or box having seams, hinges or folds, that enable opening of the packaging in a convenient manner for donning the orthopedic device 301. The packaging 300 includes a center panel 302 having a width 326 that opens opposed sides 316, 318 of the orthopedic device. The center panel 302 is sufficiently rigid to maintain a distance 324 between the opposed sides 316, 318.

The center panel 302 serves as a spine to the packaging and the width of the center panel 302 is selected to a minimal size to sufficiently maintain the sides 316, 318 of the orthopedic device apart, while minimizing a space sufficient to don the opposed sides 316, 318 on a limb. Both the distances 324, 326 are selected according to a common width of a leg upon which the orthopedic device can be applied.

The center panel 302 is bordered by first and second inner fold regions 320, 322 that permit the clinician to manipulate the packaging and hence the orthopedic device 301 according to many widths and angles according to different leg (or other limbs according to the orthopedic device) sizes as the packaging is slid underneath the leg. The fold regions offer versatility to a clinic setting and an individual wearer. The inner fold regions 320, 322 also permit the clinician to wrap and/or extend the packaging with the orthopedic device about the wearer's leg by articulating side panels 304, 306 extending from the inner fold regions 320, 322 independent of one another relative to the center panel 302.

The side panels 304, 306 generally have a width 328 closely approximating a maximum width of the widest aspect 329 of the sides of the orthopedic device. The width 328 is selected in close approximation to the widest aspect 329 to minimize the size of the packaging 300 and lead to greater compact sizing.

End panels 308, 310 extend from outer fold regions 309, 311 bordering the end panels 308, 310 and the side panels 304, 306. The end panels 308, 310 are secured to one another by a tab 314 extending from one side panel 308, which is insertable into a slot 312 generally defined along an outer fold region 309. The end panels 308, 310 preferably define indicia or instructions 331 for use with the orthopedic device 300, as described in other embodiments of this disclosure. The end panels 308, 310, when overlapping one another in a closed configuration C, as shown in FIG. 4C, generally each have the same width 330 of the preferable width 326 of the center panel 302, to create a uniformly generally rectangular packaging, which may be desirable for stocking of packaged orthopedic devices.

The end panels 308, 310, and the center panel 302 preferably define generally the same length 333, which may be shorter than a length 337 of the side panels 304, 306, in part to minimize space of the packaging, and minimize packaging when donning the orthopedic device 300. As large or cumbersome packaging may hinder donning, the packaging 300 includes panels of different lengths to minimize packaging and facilitate donning. The center panel 302 preferably has a length difference 335 at opposed ends to assure the packaging can slip under the leg or other limb better, which the length 337 of the side panels 304, 306, preferably approximates in length to the longest length aspect of the orthopedic device, while protecting the orthopedic device in storage and transit.

From the different dimensions of the panels, including length and width, the packaging offers a significantly compact structure that facilitates the donning of the orthopedic device, as it may be difficult to manipulate and articulate the packaging for donning if it is too large and if it has awkward dimensions.

Despite the illustrated means for connecting the end panels, other means may be used including other known means for fastening opposed panels of a box. The packaging 300 is preferably constructed from a same, monolithic sheet of cardboard, paperboard, corrugated plastic, or similar packaging. The sheet preferably has sufficient strength to maintain all panels erect without bending while donning the orthopedic device. Ends of the packaging may be open to limit the complexity of the packaging, particularly when the packaging is stored in a bag.

Figure 5:
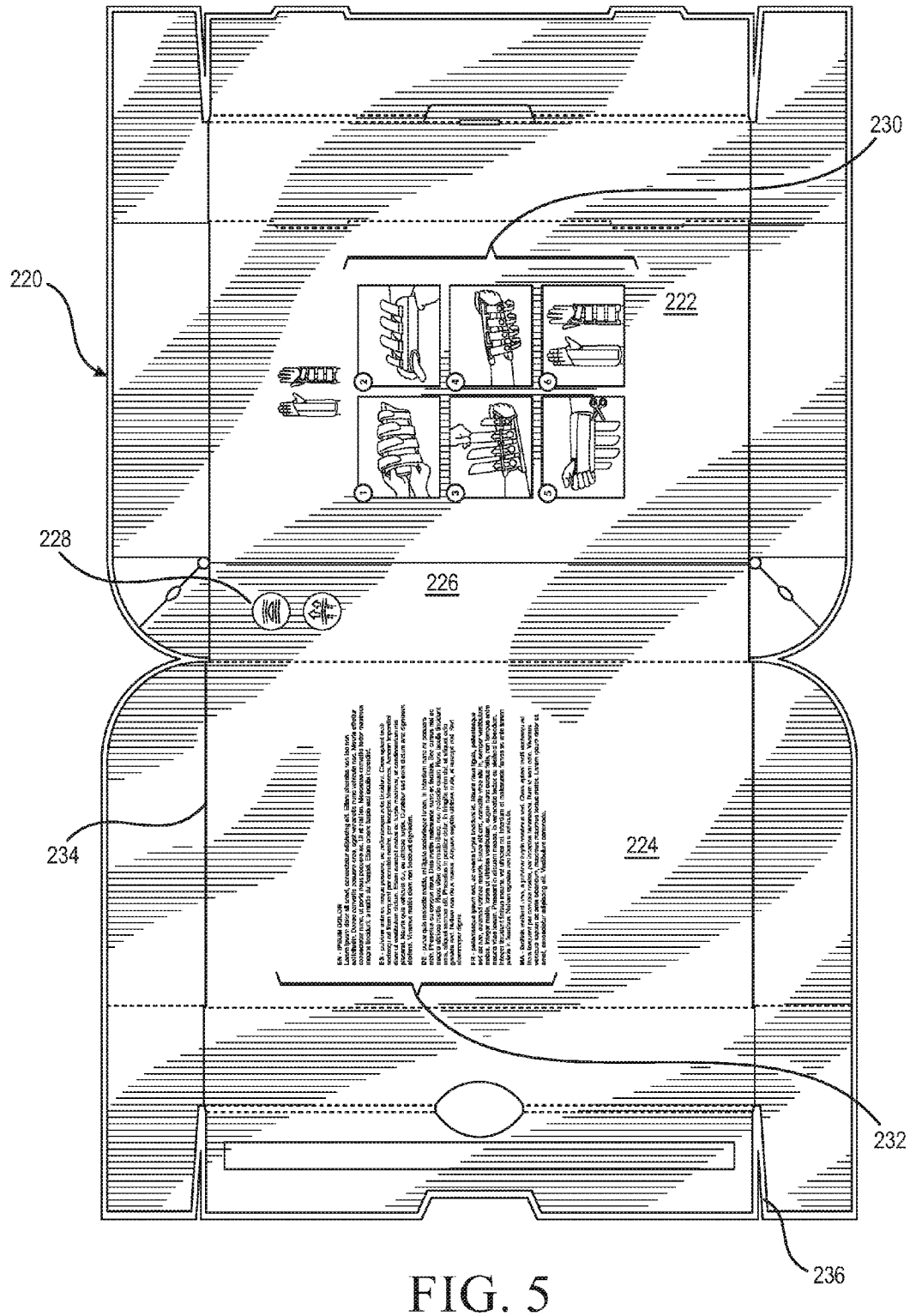
FIG. 5 is a plan view of another embodiment of donning aid packaging as a hard package in an open configuration.

FIG. 5 shows a donning aid packaging 220 arranged as a hard good. The packaging 220 has various seams and folds 234, and slits 236 for folding the packaging 220 into a closed configuration C. The packaging 220 has first and second opposing panels 222, 224 and a spine 226. Each of the panels 222, 224 and spine 226 include markings describing the article contained within the packaging 220.

The first panel 222 includes donning aids 230 arranged in a language neutral manner including a sequence for donning the article, sequential features of the article. The sequential features of the article may be a first strap, then a second strap, and so forth. Rather than search for a booklet or other form of an IFU, the wearer or clinician can merely open the packaging to see how the article is donned. There is no need for bags or instructions to accompany the packaging, and therefore there is a reduction in waste over known packaging. The second panel 224 may likewise have instructions or other relevant data 232 located and printed directly thereon. The spine 226 can include more information 228 directly printed thereon on the article located within the packaging.

Figure 6:
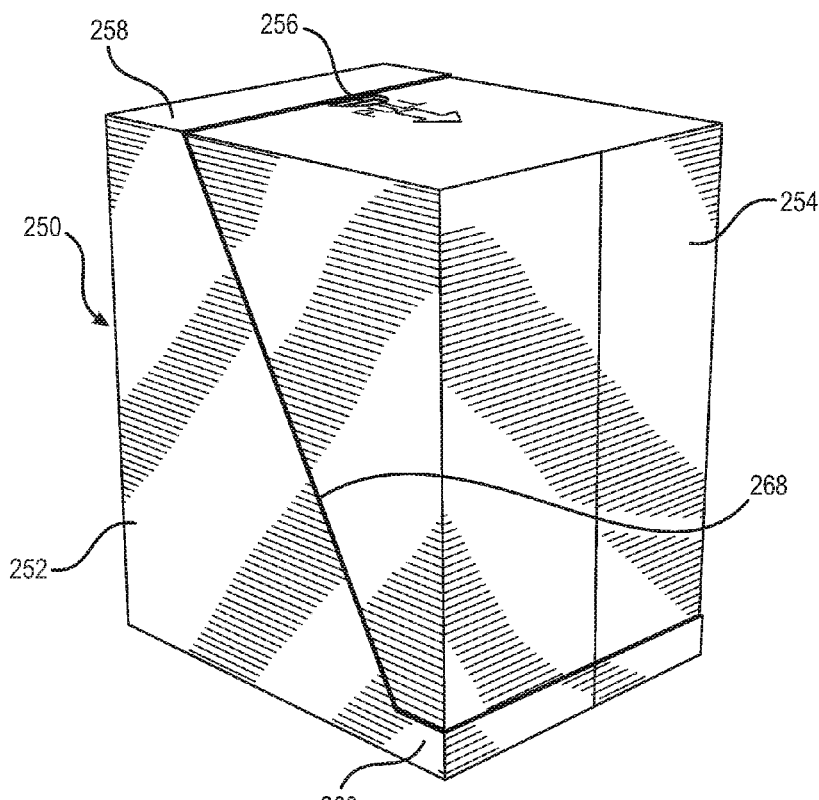
FIG. 6 is a perspective view of a packaging container for containing a plurality of donning aid packaging in a closed configuration.
Figure 7:
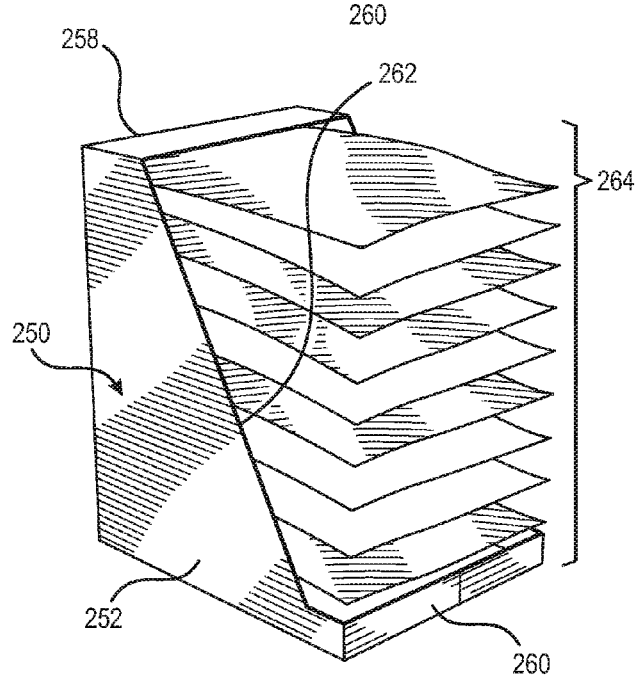
FIG. 7 is a perspective view of the packaging container of FIG. 6 in an open configuration revealing a plurality of articles stacked vertically.
Figure 8:
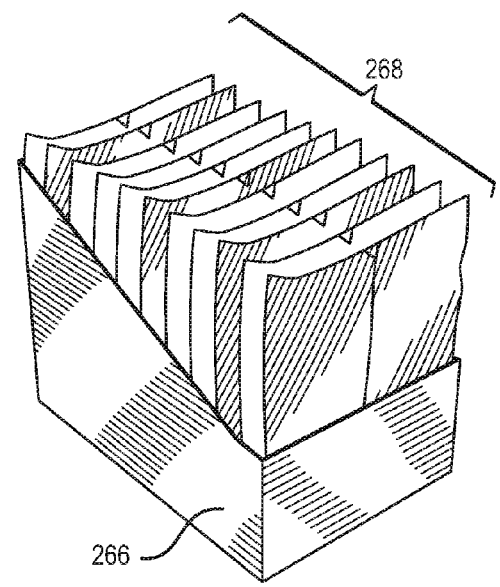
FIG. 8 is a perspective view of a variation of the packaging container of FIG. 6 in an open configuration revealing a plurality of articles stacked horizontally.

FIGS. 6-8 show embodiments of a packaging container 250 arranged for receiving a plurality of articles in donning aid packaging. Referring to FIG. 6, the container 250 includes a main portion 252 having upper and lower frame portions 258, 260. The main portion 252 and the upper and lower frame portions 258, 260 receive a detachable portion 254 that can be removed by pulling away from the main body 252. The container 250 may include a grasping feature 256, such as a tab or an opening 256, enabling a wearer to pull the detachable portion 254 away from the main body 252. The detachable portion 254 may be formed as part of the container 250 but have perforations 268 that enable easy separation of the detachable portion 254 from the main portion 252 while preserving the upper and lower frame portions 258, 260.

FIG. 7 shows the container 250 with the detachable portion 254 removed, leaving the main portion 252, and the upper and lower frame portions 258, 260. The upper frame portion 258 holds a plurality of articles 264 arranged in a vertically stacked configuration. The lower frame portion 260 serves as a bumper on the front of the container 250 to ensure the stacked 264 articles do not slide out. In this embodiment, a transition 262 between the upper and lower frame portions 258, 260 assist in retaining the articles 264 so they fall to the side. According to this embodiment, the articles 264 are in soft good packaging in the form of pouches to minimize space within the container 250.

FIG. 8 shows a variation of the container 266 whereby by the articles 268 are horizontally stacked, and the container 266 is arranged accordingly in view of the vertically stacked configuration of FIG. 7.

Figure 9:
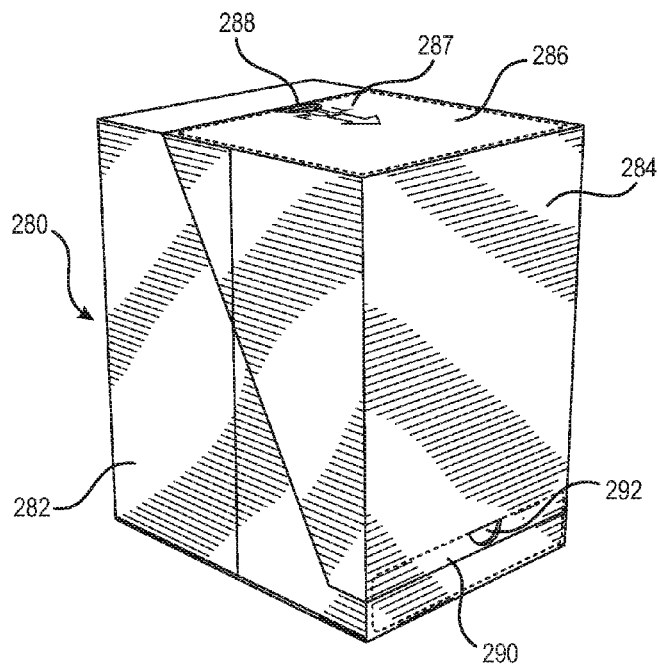
FIG. 9 is a perspective view of a variation of the packaging container of FIG. 6 in a closed configuration.
Figure 10:
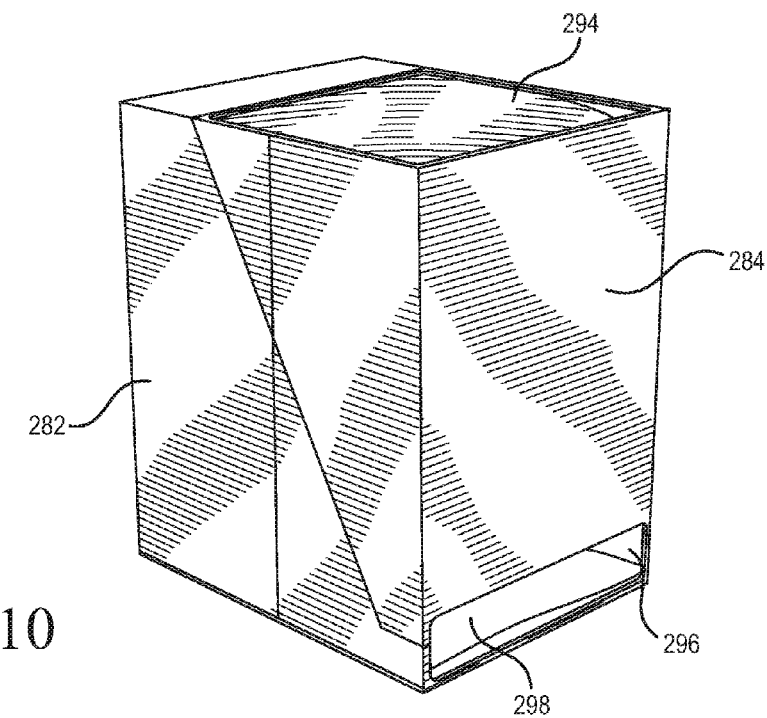
FIG. 10 is a perspective view of the packaging container of FIG. 9 in an open configuration.

FIGS. 9 and 10 exemplify another variation of the container in FIG. 6. The container 280 of FIG. 9 includes a main portion 282 and front portion 284. The front portion 284 has a removable top portion 286 and a removable bottom portion 290. Grasping features 288 and 292 are provided for removing both the top and bottom portions 286, 290. Indicia 287 is provided for showing the direction for removing the top portion 286. With the top and front bottom portions 286, 290 removed, the clinician has access through a top opening 294 and a bottom opening 296 for retrieving articles 298 from the container 280. When open, the front portion 284 remains intact with the main portion 282, and therefore possess the same integrity as in the closed configuration.

Preferably, the articles 298 are accessible from both the top opening 294, and the bottom opening 296. The bottom opening 296 is preferably sized and configured to enable the removal of a single article, whereas the top opening 294 is preferably sized and configured to enable removal of multiple orthopedic devices.

While the foregoing embodiments have been described and shown, alternatives and modifications of these embodiments, such as those suggested by others may be made to fall within the scope of the disclosure. While the donning aid packaging has for the most part been described in relation to a post-operative knee brace, it will be understood that the principles, features, and/or components described herein may be extended to packaging for other types of orthopedic and prosthetic devices, and other suitable articles not necessarily related to orthopedic and prosthetic devices.

The invention claimed is:

1. A packaging assembly arranged for holding in place an article comprising at least first and second functional features in predetermined closed and open configurations of the packaging assembly, the packaging assembly comprising:

at least two sections arranged to be secured in place relative to one another in the predetermined closed configuration of the packaging assembly, and move relative to one another in the predetermined open configuration of the packaging assembly, the at least two sections forming an inner surface defining an attachment area for receiving the article;

at least one instruction area located along the inner surface and having indicia pointing to features of the article for placement in the packaging assembly and displayed relative to the attachment area;

wherein the indicia comprise at least a first indicator and a second indicator, the first indicator arranged for corresponding to donning at least the first functional feature of the article according to a sequence of use, and the second indicator arranged for corresponding to subsequently donning at least the second functional feature of the article according to the sequence of use;

wherein the packaging assembly is arranged to support the article in a preconfigured condition for donning.

2. The packaging assembly of claim 1, further comprising a fastener located within the attachment area and arranged to secure the article within the attachment area in both the predetermined closed and open configurations.

3. The packaging assembly of claim 1, wherein the attachment area is generally centrally formed among the at least two sections and includes a marking for placing the article and a feature thereof at said marking.

4. The packaging assembly of claim 1, wherein in the closed configuration, the packaging assembly includes a longitudinal closure running along a longitudinal axis of a top face of the packaging assembly and securing the at least two sections together.

5. The packaging assembly of claim 4, wherein in the predetermined open configuration and upon opening of the closure, the at least two sections open in a bi-fold fashion.

6. The packaging assembly of claim 5, wherein in the predetermined closed configuration, the packaging assembly includes a transverse closure generally extending transversely to the longitudinal axis along transverse edges of the at least two sections.

7. The packaging assembly of claim 1, wherein the at least two sections define opposed hinges enabling the packaging assembly to be opened in a bi-fold fashion in the open configuration.

8. The packaging assembly of claim 1, wherein the at least two sections join in the closed configuration to form a handle.

9. The packaging assembly of claim 1, wherein the at least two sections define first and second side panels and a central panel, the central panel maintaining a predetermined distance between the first and second side panels, the attachment area at least coinciding with the central panel.

10. The packaging assembly of claim 1, wherein the indicia of the at least one instruction area is directly located on the inner surface of the at least two sections.

11. The packaging assembly of claim 10, wherein the indicia is arranged on the at least two sections in a sequential manner corresponding to sequential features of the article.

12. The packaging assembly of claim 1, wherein the at least one instruction area defines lead lines located on the at least two sections aligning the indicia to features of the article.

13. The packaging assembly of claim 1, further comprising at least one positioning element connecting to the at least two sections and adapted to maintain the article in a fixed position relative to the at least two sections.

14. The packaging assembly of claim 1, wherein the at least two sections have edges secured to one another in the predetermined closed configuration, and the edges are separated from one another in the predetermined open configuration.

15. The packaging assembly of claim 14, wherein the indicia is selected from the group consisting of numbering, lettering, geometric elements, text, and lead lines.

16. A method for donning an article comprising at least first and second functional features, comprising the steps of:
    placing the article in a packing assembly having at least two sections arranged to be secured in place relative to one another in a closed configuration, and move relative to one another in an open configuration, the at least two sections forming an inner surface defining an attachment area for receiving the article;
    placing the article in the attachment area in a preconfigured condition for donning;
    providing at least one instruction area located along the inner surface and having indicia pointing to features of the article;
    providing at least a first indicator and a second indicator; and
    following the first indicator and donning at least the first functional feature of the article corresponding to the first indicator arranged in a sequential notation on the inner surface and according to a sequence of use, and then following the second indicator and donning at least the second functional feature of the article corresponding to the second indicator arranged in the sequential notation on the inner surface and according to the sequence of use.

17. The method of claim 16, further comprising securing the at least two sections along their longitudinal edges.

18. A packaging assembly containing an article comprising at least first and second functional features and secured at a predetermined location relative to the packaging assembly in closed and open configurations of the packaging assembly, the packaging assembly comprising:
    at least two sections arranged to be secured in place relative to one another in the closed configuration, and move relative to one another in the open configuration, the at least two sections forming an inner surface defining an attachment area upon which the article is secured;
    at least one instruction area located along the inner surface and having indicia comprising at least first and second indicators pointing to the at least first and second functional features of the article, respectively, for placement in the packaging assembly, the at least one instruction area being located relative to an attachment area displayed by the at least two sections and the article having a feature corresponding to and secured to the attachment area at a marking in both the closed and open configurations;
    at least one closure is arranged to secure edges of the at least two sections to one another in the closed configuration;
    wherein the indicia represents a sequence of steps for utilizing a sequence of the at least first and second functional features of the article;
    wherein the article is secured to the at least two sections such that the article is stabilized in the open configuration of the packaging assembly in an open configuration of the article;
    wherein the packaging assembly is arranged to support the article in a preconfigured condition for donning.

\* \* \* \* \*